US00PP37389P3

(12) United States Plant Patent
Boos

(10) Patent No.: US PP37,389 P3
(45) Date of Patent: Apr. 28, 2026

(54) NECTARINE TREE NAMED 'Prima Diamond 7'

(50) Latin Name: *Prunus persica nucipersica*
Varietal Denomination: Prima Diamond 7

(71) Applicant: Threefold Holdings Group, LLC, Reedley, CA (US)

(72) Inventor: Nicholas S. Boos, Clovis, CA (US)

(73) Assignee: Threefold Holdings Group, LLC, Reedley, CA (US)

( * ) Notice: Subject to any disclaimer, the term of this patent is extended or adjusted under 35 U.S.C. 154(b) by 0 days.

(21) Appl. No.: 18/445,881

(22) Filed: Mar. 1, 2024

(65) Prior Publication Data

US 2025/0280746 P1 Sep. 4, 2025

(51) Int. Cl.
*A01H 6/74* (2018.01)
*A01H 5/08* (2018.01)

(52) U.S. Cl.
USPC ..... Plt./190

(58) Field of Classification Search
USPC ..... Plt./190
CPC ..... A01H 6/7454; A01H 5/08
See application file for complete search history.

(56) References Cited

U.S. PATENT DOCUMENTS

PP12,011 P2 7/2001 Gerawan
PP12,418 P2 2/2002 Zaiger et al.

*Primary Examiner* — Keith O. Robinson
(74) *Attorney, Agent, or Firm* — Michelle Bos Legal LLC

(57) ABSTRACT

A new and distinct variety of nectarine tree (*Prunus persica nucipersica*), which is denominated varietally as 'Prima Diamond 7', and which produces large fruits that mature approximately the last week of June in the San Joaquin Valley of Central California.

2 Drawing Sheets

Botanical designation: *Prunus persica nucipersica.*
Varietal denomination: 'Prima Diamond 7'.

BACKGROUND OF THE NEW VARIETY

The present variety of nectarine tree resulted from an on-going program of fruit and rootstock breeding. The purpose of this program is to improve the commercial quality of deciduous fruit varieties and rootstocks by creating and releasing promising selections of *Prunus* species. To this end, both controlled and hybrid cross pollinations are made each year to produce seedling populations from which improved progenies are evaluated and selected.

The seedling 'Prima Diamond 7' was originated by the breeders and selected from a population of seedlings growing in the experimental orchards located in the San Joaquin Valley of California. The seedlings, grown on their own roots, were derived from planting seed of the variety 'Prima Diamond 19' (U.S. Plant Pat. No. 12,011 P2), which was a yellow-fleshed nectarine used as the female parent. The pollen parent of this seedling was from the variety 'Honey Fire' nectarine tree (U.S. Plant Pat. No. 12,418 P2). The resulting fruit was collected from the female parent at a mature stage and seeds were extracted. After a period of stratification, the seed was placed in the greenhouse by population, and then field planted for tree establishment, and ultimately to exhibit fruit for evaluation. One yellow-fleshed nectarine seedling, which is the present variety, exhibited especially desirable characteristics, and was then designated as 'Prima Diamond 7'.

ASEXUAL REPRODUCTION

Asexual reproduction of this new and distinct variety of nectarine tree was accomplished by budding the new nectarine tree onto trees of 'Nemaguard' Rootstock (unpatented). This was performed in an experimental orchard located in the San Joaquin Valley of California. Subsequent evaluations of these asexually reproduced plants have shown those asexual reproductions run true to the original tree. All characteristics of the original tree and its fruit were established and appear to be transmitted through these succeeding asexual propagations.

SUMMARY OF VARIETY

'Prima Diamond 7' is a new and distinct variety of nectarine tree, which is considered of relatively large size, and which has a vigorous growth characteristic. This new tree is also a regular and productive bearer of relatively large, firm, yellow-fleshed, low acid fleshed tight freestone fruit which have a very good flavor and eating qualities.

The variety was discovered in a seedling population from a controlled cross of the nectarine variety 'Prima Diamond 19' (U.S. Plant Pat. No. 12,011 P2), which was the seed parent, and the nectarine variety 'Honey Fire' (U.S. Plant Pat. No. 12,418 P2), which was the pollen parent. A promising seedling was budded onto 'Nemaguard' (unpatented) rootstocks. The resulting clonally reproduced trees of the current variety have been consistent in phenology with the performance of the original seedling. The seed parent 'Prima Diamond 19' produces clingstone fruits that mature for commercial harvest approximately in that last week of June under the climatic conditions in the San Joaquin Valley of Central California. In relative comparison to the seed parent, the current variety ripens more than 12 days earlier. Additionally, the current variety produces fruit that is about 4.0 mm to about 5.0 mm larger in equatorial circumference compared to the seed parent. This increase in fruit size results in increased fruit production over the female parent variety. Further, the current variety exhibits lower flesh acidity (approximately 0.45 titratable acidity) than the female parent (which has an approximate 0.70 titratable acidity). In relative comparison to the pollen parent, the current variety ripens more than 7 days later. The pollen parent 'Honey Fire' produces fruit with a low acid profile, while the fruit of 'Prima Diamond 7' has a higher acidity level more in keeping with a typical nectarine flavor. 'Prima Diamond 7' fruit is further distinguished from fruit of the pollen parent by its equatorial diameter, which is about 7 to 10 mm larger than that of 'Honey Fire'.

Figure 1:
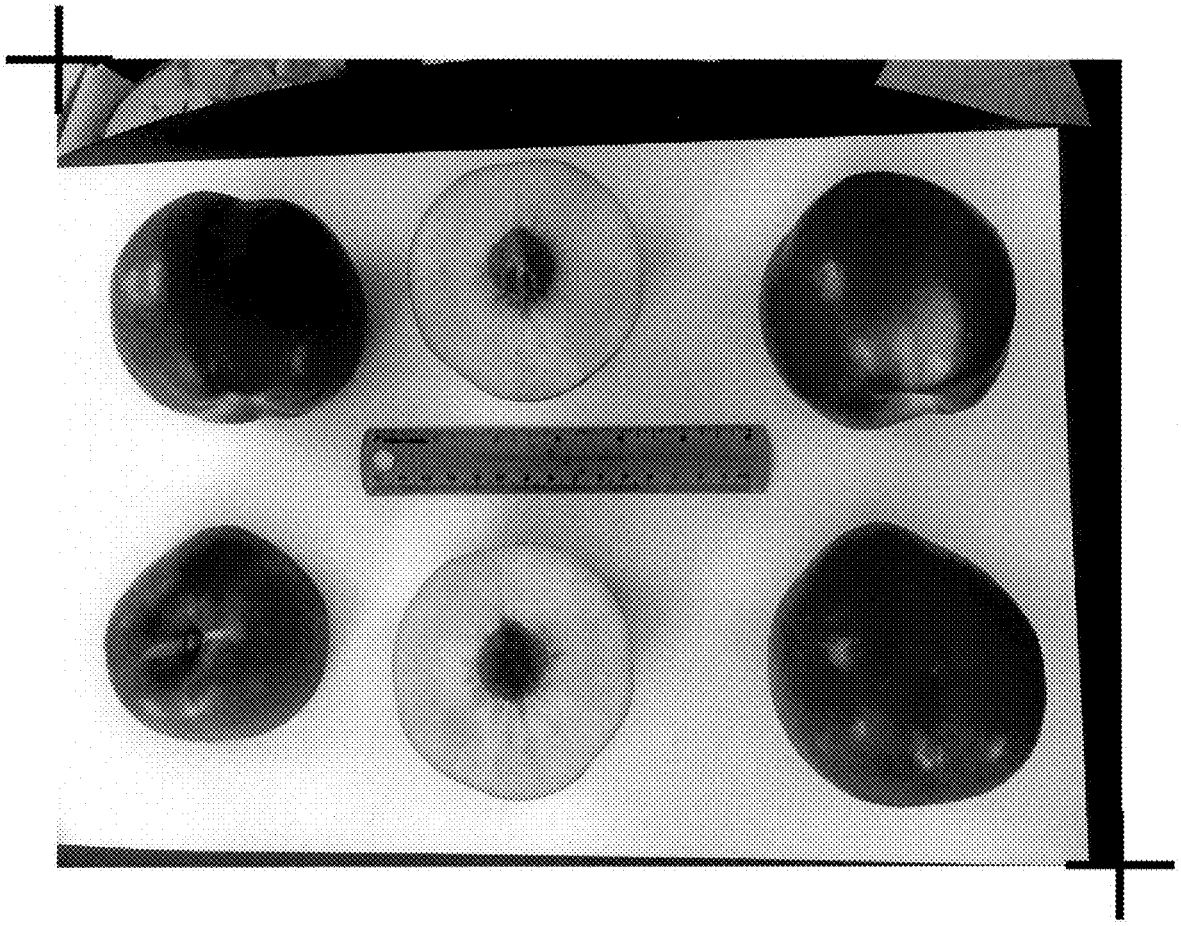
FIG. 1 is a color photograph of five pieces of characteristic fruits sufficiently matured for harvest. The aspects of the fruit are positioned to display the apical (bottom, left), basal (bottom, right), lateral (top, left), and sutorial (top, right) vantages. Additionally, one fruit is bisected at the equatorial plane and placed so that the internal flesh and its characteristics can be observed (middle, top and bottom).
Figure 2:
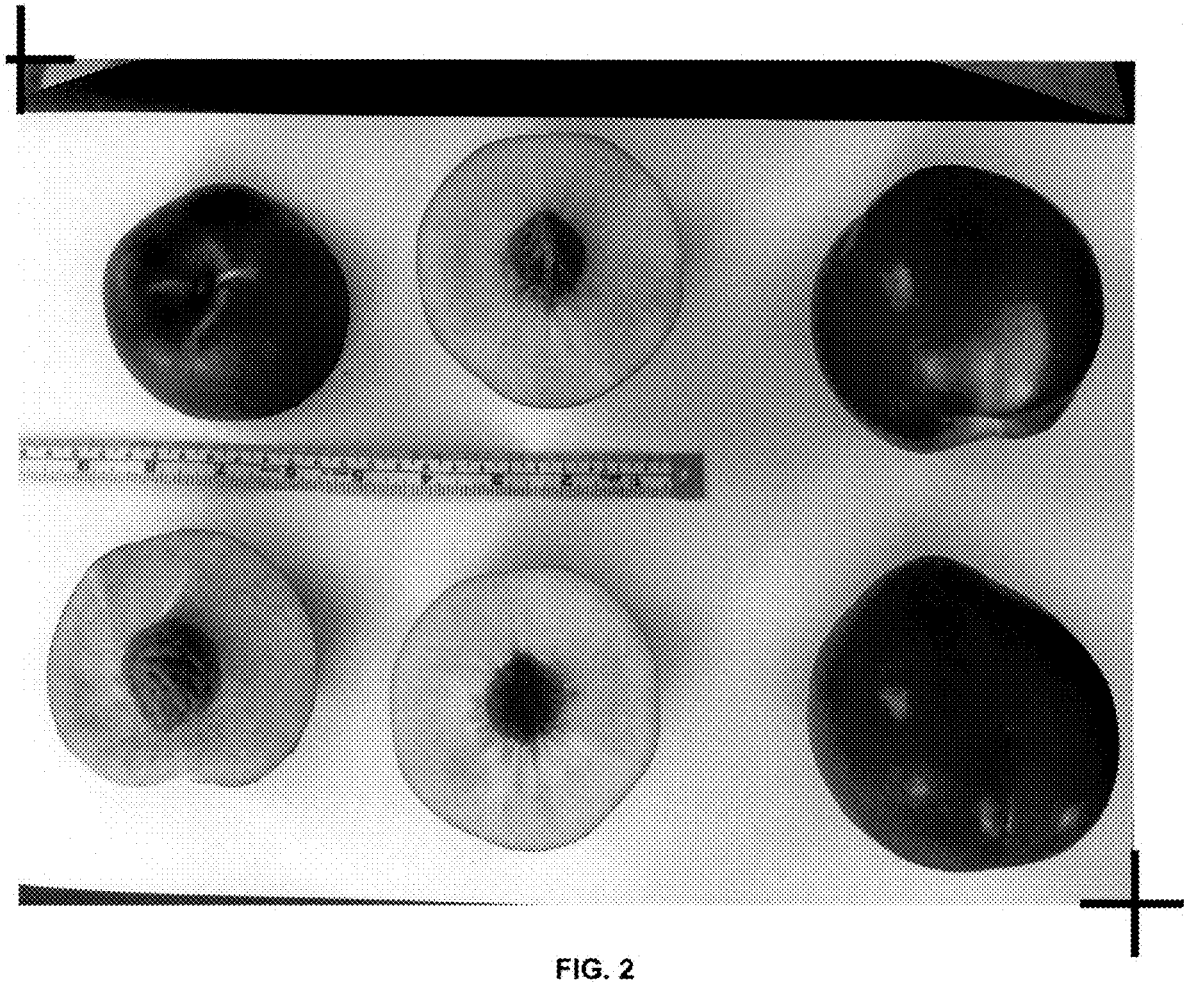
FIG. 2 is another color photograph of the fruit. Intact fruit is shown from the apical (top, left), sutorial (top, right), and basal (bottom, right) vantages. Two fruit are bisected at either the equatorial plane (middle, top and bottom) or lateral plane (bottom, left) to display the internal flesh.

The colors in these photographs are as nearly true as is reasonably possible in a color representation of this type. Due to chemical development, processing and printing, the fruit depicted in these photographs may, or may not, be accurate when compared to the actual specimen. For this reason, future color references should be made to the color plates (Royal Horticultural Society, Fourth Edition, 2001) and descriptions provided.

NOT A COMMERCIAL WARRANTY

The following detailed description has been prepared to solely comply with the provisions of 35 U.S.C. § 112, and does not constitute a commercial warranty (either expressed or implied) that the present variety will in the future display all the botanical, pomological, or other characteristics as set forth hereinafter. Therefore, this disclosure may not be relied upon to support any future legal claims including, but not limited to, breach of warranty of merchantability, fitness for any purpose, or non-infringement which is directed, in whole or in part, to the present variety.

DETAILED DESCRIPTION

Referring more specifically to the pomological details of this new and distinct variety of nectarine tree, the following has been observed in five-year-old trees and under the ecological conditions prevailing at the orchards located within Fresno County in the Central San Joaquin Valley. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Variable. Generally ranges from about 3.5 m to about 4.0 m in height and from about 3.5 m to about 4.3 m in width at maturity. Tree size can vary with crop load and the conditions under which the fruit and tree are grown.

*Width*.—About 3.5 m to about 4.3 m at maturity.

*Vigor*.—Considered vigorous when compared to normal growth expectations in this region The current variety has been propagated on 'Nemaguard' peach rootstock. The present nectarine tree variety grew from about 280 cm to about 290 cm in height during the first growing season. The new variety was pruned to a height of about 250 cm during the first dormant season.

*Productivity*.—Very productive when compared to nectarine tree varieties than ripen within the same maturity period. The number of the fruit set varies with the prevailing climatic conditions and the cultural practices employed.

*Fruit bearing*.—The tree has consistently produced an abundance of flower buds that result in high fruit sets and heavy, consistent yields.

*Tree form*.—Upright to spreading.

*Density*.—Average branching pattern and canopy density for the species.

*Winter hardiness*.—No winter injury has been observed during the last five years of evaluation in the Central San Joaquin Valley. The current variety has not been intentionally subjected to drought, heat stress, or exposed to conditions that result in flower and fruitlet damage due to frost in the late winter and early springtime period.

Trunk:

*Size*.—Medium to medium large. Trunk circumference averaged about 55.0 cm when measured at a height above the soil level of 25.0 cm after the fifth growing season.

*Bark texture*.—Rough and vertically furrowed in texture at maturity.

*Lenticels*.—Lenticels are numerous, about 10 to 12 per cm2, and medium in size. The average width is from about 5.0 mm to about 7.0 mm, and the average height is from about 3.0 mm to about 4.0 mm.

*Lenticel color*.—Considered orange-brown (RHS Greyed-Orange Group N170 A).

*Bark coloration*.—Considered a medium grey-brown (RHS Greyed-Orange Group 166 A).

Primary branches:

*Size*.—Considered slightly above average for the variety.

*Circumference*.—The branch circumference average is about 30.0 cm when measured 15.0 cm from the trunk attachment.

*Flowering shoot thickness*.—Flowering shoot thickness averages about 5.0 mm when measured on annual growth.

*Surface texture*.—Shoot texture is considered smooth during the early growth period. As lenticles begin to form later in the season, the shoot texture is less smooth.

*Crotch angles*.—Moderately upright. Primary limbs range from about 47 degrees to about 50 degrees above the horizontal plane.

*Current season shoots*.—Surface texture-Relatively smooth.

*Internode length*.—When measured at the mid-shoot, the internodal distances average about 2.4 cm.

*Color of mature branches*.—Medium brown (RHS Greyed-Orange 176 C).

*Current season's shoots*.—Color — Light green (RHS Yellow-Green Group 145 A). The color of new shoot tips is considered a bright and shiny green (RHS Yellow-Green Group 144 B).

Leaves:

*Size*.—Considered medium large for the species.

*Leaf length*.—About 15.0 cm to about 19.0 cm (including the petiole).

*Leaf width*.—About 3.5 cm to about 4.6 cm.

*Leaf base*.—Shape — Crenate.

*Leaf form*.—Lanceolate.

*Leaf tip form*.—Accurate

*Leaf color*.—Upper Leaf Surface-A dark green (approximately RHS Green Group 137 A).

*Leaf texture*.—Upper Leaf Surface — Glabrous. Lower Leaf Surface — Glabrous.

*Leaf color*.—Lower Leaf Surface-Medium green (RHS Green Group 137 B).

*Leaf venation*.—Pinnately veined.

*Mid-vein*.—Color-Considered a light green (RHS Greyed-Green Group 193 A).

*Leaf margins*.—Slightly undulating. Form — Finely crenulate. Uniformity — Generally uniform and gently undulating.

*Leaf petioles*.—Form — Canunculate. Length — About 10.0 to about 12.0 mm. Thickness — About 2.0 mm. Color — Pale green (RHS Yellow-Green Group 145B). Texture — Glabrous. Strength — Durable.

*Leaf glands*.—Size — About 1.0 mm to about 1.5 mm in length, and about 1.0 mm in width. Number — Normally 2 to 3 glands per margin side. Type — Glands located at the base of the leaf are predominantly reniform in shape. Color — Considered a pale orange (RHS Greyed-Orange Group N163B).

*Leaf stipules*.—Size — Medium large for this variety. Length — About 6.0 mm to about 8.0 mm. Width — About 1.0 mm. Number — Typically, 2 to 6 per active shoot tip. Form — Lanceolate and with serrated margin. Color — Green (RHS Green Group 143 C).

Flower buds:

*Hardiness*.—No winter injury (bud death) has been noted during the last five years of observation in the central San Joaquin Valley. The new variety of nectarine tree has not been intentionally subjected to drought, cold, or heat stress, and, therefore, this information is not available.

*Flower bud*.—Generally — Depending upon the stage of development, the floral buds are about 7.0 mm wide, about 10.0 mm long, conic in form, and slightly appressed relative to the bearing shoot. The diameter is about 4.0 mm to about 5.0 mm. Color — This characteristic is dependent upon the proximity to the bloom. The bud scales are deep purple (approximately RHS Greyed-Purple Group N186 C). The buds are considered hardy under typical central San Joaquin Valley climatic conditions. Surface Texture — Satiny texture. Not glabrous. Orientation — Slightly appressed in an apical orientation.

*Flower pedicel*.—Length — Considered medium and having an average length of about 3.0 mm to about 3.5 mm. Strength — Tenacious. Diameter — Considered average, about 2.0 mm. Color — A light green (RHS Greyed-Yellow Group 160 C). Texture — Very light pubescence.

Flowers:

*Date of first bloom*.—Approximately Feb. 21, 2022. Blooming time — The date of full bloom was observed on Mar. 1, 2022. The date of full bloom varies slightly with climatic conditions and prevailing cultural practices. Duration of Bloom — Approximately 12 days. This characteristic varies slightly with the prevailing climatic conditions.

*Flower class*.—Perfect flower form.

*Flower type*.—The variety is considered to have a showy type flower.

*Flower size*.—Considered medium large; diameter about 22 mm to 25 mm; depth about 21 mm to 23 mm from basal end of calyx to peripheral portion of open flower petals.

*Bloom quantity*.—Abundant.

*Flower bud density*.—Dense. Flower Bud Frequency — Normally, 1 flower bud per fruiting node, but multiple flower buds are often present.

*Petal size*.—Generally considered medium-large for the species. Petal length — About 20.0 mm to about 22.0 mm. Petal width — About 19.0 mm to about 20.0 mm.

*Petal form*.—Generally round.

*Petal count*.—Five flower petals per bloom with almost no exceptions.

*Petal texture*.—Satiny. Upper Petal Texture — Very slight pubescence. Lower Petal Texture — Very slight pubescence.

*Petal color*.—Considered light pink on the upper surface (RHS Red-Purple Group 62 C) and pale pink (RHS Red-Purple Group 62 D) on the lower surface.

*Fragrance*.—Slightly aromatic; typical of nectarine.

*Petal claw*.—Form — The claw is considered generally ovoid and has a medium size when compared to other varieties. Length — About 12.0 mm to about 14.0 mm. Width — About 10.0 mm to about 12.0 mm.

*Petal margins*.—Generally considered variable, from nearly smooth to slightly ruffled, and considered moderately undulate.

*Petal apex*.—Rounded without an apical notch.

*Floral nectaries*.—Color — Considered a dull orange (RHS Greyed-Orange 172 A).

*Calyx*.—Color — Considered a grey red color (RHS Greyed-Red 178 A).

*Sepals*.—External Surface Texture — A short fine pubescence. Internal Surface Texture — Nearly glabrous. Number — Nearly always 5. Size — Moderately large. Sepal Length — About 3.5 mm. Sepal Width — About 3.0 mm. Sepal Shape — Ovate in form. Sepal Margin — Smooth. Sepal Color — A dark purple (RHS Greyed-Purple Group N186 C).

*Stamen*.—Number — About 30 to 40.

*Anthers*.—Generally — Generally oval in form. Color — Generally considered a pale yellow depending on maturity. (Approximately RHS Greyed-Yellow 160 B). Position Relative to Stigma — About 1.0 mm to about 1.5 mm superior to the floral stigma.

*Pollen production*.—Pollen is abundant and has a yellow color. (RHS Yellow-Orange Group 17 C).

*Fertility*.—Self-fertile.

*Filaments*.—Size — Variable, with about 12.0 mm to about 16.0 mm in length. Color — A very pale pink (RHS Red Group 56 D).

*Pistil*.—Number — Nearly always 1 pistil per floral bud. Occasionally more than 1 are observed. Generally — Considered moderately long in size. Length — Averages about 19.0 mm (including the ovary, style, and stigma). Diameter — About 1.0 mm, excluding the ovary. Color — Considered a very pale green (approximately RHS Yellow-Green Group 150 D). Surface Texture — The variety has a long glabrous pistil. Position Relative to Petals — Relatively perpendicular to the petal plane at full bloom. Ovary Surface Texture — Glabrous.

Fruit:

*Maturity when described*.—Firm ripe condition (shipping ripe).

*Date of first picking*.—Typically, harvest begins on or about June 24 in the Central San Juaquin Valley.

*Date of last picking*.—Approximately July 12. The date of harvest can vary with the prevailing climatic conditions, crop loads, and the current climatic and cultural practices.

*Size*.—Large; diameter 75 mm to 78 mm; height 77 mm to 80 mm.

*Typical Weight*.—About 240 grams to about 268 grams. The fruit size and weight can vary and are dependent on the prevailing cultural practices and growing conditions.

*Fruit firmness*.—Classed as a firm-melting flesh type.

*Titratable acidity*.—Approximately 0.45.

*Fruit shape*.—Generally-Considered round to slightly ovoid.

*Fruit suture shape*.—Sutural lobing can be observed where the lateral hemispheres are slightly unequal.

*Apex*.—Shape — Rounded to retuse.

*Base*.—Shape — Considered round to slightly ovoid.

*Stem cavity*.—Ovoid in form. Considered moderately shallow.

*Fruit skin*.—Thickness — Skin is relatively thick. Surface Texture — Glabrous. Conspicuousness of Lenticels — Typically, a low presence of surface lenticles are noted but occasionally can be observed nearer the apex of the fruit surface. Taste — Considered a sweet and low acidic flavor. Tendency to crack — Cracking has not been observed.

*Fruit skin color*.—Blush Color — A deep, bright red (RHS Red Group 46 B). The blush of the fruit typically covers approximately 90% of the fruit skin surface.

*Ground color*.—A medium yellow (RHS Yellow Group 13 C).

*Fruit glossiness*.—Considered moderate in luster.

*Fruit stem*.—Size — About 6.0 mm in length. Diameter — About 2.5 mm to about 3.0 mm. Color — A medium brown (RHS Grey-Brown Group 199 A).

*Fruit flesh*.—Ripening — Considered average in ripening rate post-harvest. Texture — Considered dense and moderately firm. (Firm-melting flesh class) Fibers — Very fine. Aroma — Faint, pleasant. Eating Quality — Sweet and mild. Flavor — Considered sweet and mild profile. Juice Production — Moderate. Brix — About 13.0 to about 14.9 Brix. Acidity — Not high in acidity. Considered a mid to lower acidic fruit flesh. Approximately 0.45 titratable activity. Flesh Color — It is considered a yellowish orange (RHS Yellow Group 12 A).

Stone:

*Type*.—Clingstone.

*Size*.—It is generally considered to be relatively small in relation to the fruit size.

*Length*.—Medium-small for the species at about 40.0 mm.

*Width*.—About 26.0 mm.

*Depth*.—About 21.0 mm.

*Form*.—Ovoid in form.

*Stone base*.—Shape-Uniform with a blunted base.

*Apex*.—Shape — A small acute tip exists at the apex.

*Stone surface*.—Surface Texture — Moderately pitted toward the base. Irregularly furrowed toward the apical end. Pitting is abundant, typically more noted on the lateral sides, and toward the basal end of the stone. Ridges — The surface texture is generally characterized by more prominent ridges along the ventral edges. Ventral edge — Width-Considered medium and having a dimension of about 4.0 mm to about 5.0 mm when measured at the mid-suture. Dorsal edge — Shape-Full, lightly grooved, and having a reasonably smooth margin.

*Stone color*.—Considered a reddish brown (RHS Greyed-Red Group 181 B).

*Tendency to split*.—Not noted as characteristic of the current variety.

*Kernel*.—Length — About 20 mm. Width — About18 mm. Thickness — About 4.0 mm to about 6.0 mm. Form — Considered ovoid. Apex shape — A blunted apex. Pellicle — Surface Texture-Pubescent. Taste — Bitter. Color — A pale brown (RHS Greyed-Orange Group 167 B).

*Use*.—The present variety 'Prima Diamond 7' is considered to be a nectarine tree that matures fruit for commercial harvest during the last week of June when grown in the Central part of the San Joaquin Valley of California. The fruit of the current variety is a yellow-fleshed clingstone with large fruit expression, attractive external blush, and a sweet mild flavor, which are useful characteristics for both local and long distance shipping and fresh market consumption.

*Keeping quality*.—Excellent. Fruit has stored well for 25 days after harvest when stored properly at 1.0 degrees Celsius.

*Shipping quality*.—Good. The fruit of the new nectarine tree variety showed minimal bruising of the flesh or skin damage after being subjected to normal professional commercial harvesting and packing procedures.

*Resistance to insects and disease*.—No susceptibilities were noted. The present variety has not been intentionally tested to expose or detect any susceptibilities or resistances to any known plant, fruit diseases, insect, frost, winter injury, or other environmental factors.

Although the new variety of nectarine tree possesses the described characteristics when grown under the ecological conditions prevailing in the Central part of the San Joaquin Valley of California, it should be understood that variations of the usual magnitude and characteristics incident to changes in growing conditions, fertilization, pruning, pest control, and horticultural management are to be expected.

The invention claimed is:

1. A new distinct variety of nectarine tree named 'Prima Diamond 7' substantially as illustrated and described, and which is characterized principally as to novelty by producing an attractively colored yellow-fleshed, tight freestone nectarine which is mature for harvesting and shipment approximately June 24 to July 12 under the ecological conditions prevailing in the San Joaquin Valley of central California.

* * * * *